US00PP11176P

United States Patent [19]

May

[11] Patent Number: Plant 11,176

[45] Date of Patent: Jan. 11, 2000

[54] CHRYSANTHEMUM PLANT NAMED 'ORANGE POMONA'

[75] Inventor: James D. May, Carlsbad, Calif.

[73] Assignee: Yoder Brothers, Inc., Barberton, Ohio

[21] Appl. No.: 09/112,336

[22] Filed: Jul. 9, 1998

[51] Int. Cl.[7] ..... A01H 5/00

[52] U.S. Cl. ..... Plt./290

[58] Field of Search ..... Plt./290, 287

[56] References Cited

U.S. PATENT DOCUMENTS

P.P. 7,850 3/1992 VandenBerg ..... Plt./293

*Primary Examiner*—Howard J. Locker

*Attorney, Agent, or Firm*—C. A. Whealy

[57] ABSTRACT

A distinct cultivar of Chrysanthemum plant named 'Orange Pomona', characterized by its uniformly mounded plant habit; freely branching habit; dark green foliage; uniform flowering; large decorative disbud-type inflorescences that are about 10 cm in diameter; attractive ray florets that change from red to orange with development; and good postproduction longevity with inflorescences and leaves maintaining good substance and color for about three weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Orange Pomona.

The new cultivar was discovered by the Inventor in February, 1995, in a controlled environment in Encinitas, Calif., as a naturally-occurring mutation of the Chrysanthemum cultivar Pomona (disclosed in U.S. Plant Pat. No. 6,802). The new cultivar was observed as a single plant within a population of flowering plants of the parent cultivar. The selection of this plant was based on its orange ray floret color.

Asexual reproduction of the new Chrysanthemum by terminal cuttings harvested in a controlled environment in Carlsbad, Calif., has shown that the unique features of this new Chrysanthemum are stable and reproduced true to type in successive generations.

SUMMARY OF THE INVENTION

The cultivar Orange Pomona has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Orange Pomona'. These characteristics in combination distinguish 'Orange Pomona' as a new and distinct Chrysanthemum:

1. Uniformly mounded plant habit.
2. Freely branching habit, dense plants.
3. Dark green foliage.
4. Uniform flowering.
5. Relatively large decorative disbud-type inflorescences that are about 10 cm in diameter.
6. Attractive ray florets that change from red to orange with development.
7. Good postproduction longevity with inflorescences and leaves maintaining good substance and color for about three weeks in an interior environment.

Plants of the new Chrysanthemum are similar to plants of the cultivar Cherry Pomona (U.S. Plant Pat. No. 7,850) in most horticultural characteristics with the exception of ray floret color. Ray floret color of plants of the new Chrysanthemum changes from red to orange (45A to 42B to 34A, fading to 35A to 35B with yellowish undertones, close to 11B) whereas ray floret color of plants of 'Cherry Pomona' is cherry red (45A to 53C).

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Orange Pomona'.

The photograph at the bottom of the first sheet is a close-up view of a typical inflorescence of a plant of 'Orange Pomona'.

The photograph at the top of the second sheet is a close-up view of upper and lower surfaces of typical inflorescences (top) and leaves (bottom) of plants of 'Orange Pomona'.

The photograph at the bottom of the second sheet comprises a side perspective view of typical plants of 'Orange Pomona' (left) and 'Cherry Pomona' (right) showing the differences in ray floret color. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Orange Pomona.

Commercial classification: Decorative disbud-type pot chrysanthemum.

Parentage: Naturally-occurring mutation of *Dendranthema grandiflora* cultivar Pomona, disclosed in U.S. Plant Pat. No. 6,802.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Perennial herbaceous decorative disbud-type pot Chrysanthemum. Upright, inverted triangle. Stems initially upright, then somewhat spreading giving a uniformly mounded appearance to the plant. Freely branching; about four lateral branches develop after removal of terminal apex (pinching), dense and full plants.

*Plant height*.—About 24 cm.

*Plant width*.—About 40 cm.

*Foliage description*.—Arrangement: Alternate. Length: About 7.1 cm. Width: About 5.2 cm. Apex: Mucronate. Base: Attenuate. Margin: Palmately lobed, sinuses between lateral lobes parallel. Texture: Upper and lower surfaces slightly pubescent, very fine white hairs. Veins prominent on lower surface. Petiole length: About 1.6 cm. Color: Young foliage upper surface: Darker than 147A. Young foliage lower surface: Darker than 147B. Mature foliage upper surface: 147A. Mature foliage lower surface: Close to 147B. Venation upper surface: 147A to 147B. Venation lower surface: 147B.

Inflorescence description:

*Appearance*.—Decorative disbud-type inflorescence form with oblong-shaped ray florets. Inflorescences borne on terminals above foliage, arising from leaf axils. Disk and ray florets arranged acropetally on a capitulum.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about nine weeks later.

*Postproduction longevity*.—Inflorescences and leaves will maintain good color and substance for about three weeks in an interior environment.

*Quantity of Inflorescences*.—As a disbud-type, all flowering stems are removed but one to maximize inflorescence size. About four inflorescences per plant.

*Inflorescence bud*.—Height: About 7 mm. Diameter: About 8 mm. Color: Close to 141A.

*Inflorescence size*.—Diameter: About 10 cm. Depth (height): About 4.6 cm. Diameter of disc: About 6 mm, inconspicuous.

*Ray florets*.—Shape: Oblong with very short corolla tube. Aspect: Straight, flat to convex. Length: About 4.7 cm. Width: About 1.2 cm. Apex: Rounded to acute. Margin: Entire. Texture: Smooth, glabrous. Number of ray florets per inflorescence: Numerous, about 157. Color: When opening, upper surface: Close to 46A, then 45A. When opening, lower surface: Close to 172A, then 11A. Fully opened, upper surface: 45A to 42B to 34A, fading to 35A to 35B with yellowish undertones, close to 11B. Fully opened, lower surface: 11A to close to 11B to 11C.

*Disc florets*.—Shape: Tubular. Apex: Dentate. Length: About 7 mm. Width, apex: About 2 mm. Width, base: About 1 mm. Number of disc florets per inflorescence: Few, about 12. Color: Immature: 144A to 154A. Mature: Apex: 9A. Mid-section and base: White.

*Reproductive organs*.—Androecium: Present on disc florets only. Anther color: 9A. Pollen amount: Moderate Pollen color: 12A. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Orange Pomona', as illustrated and described.

* * * * *

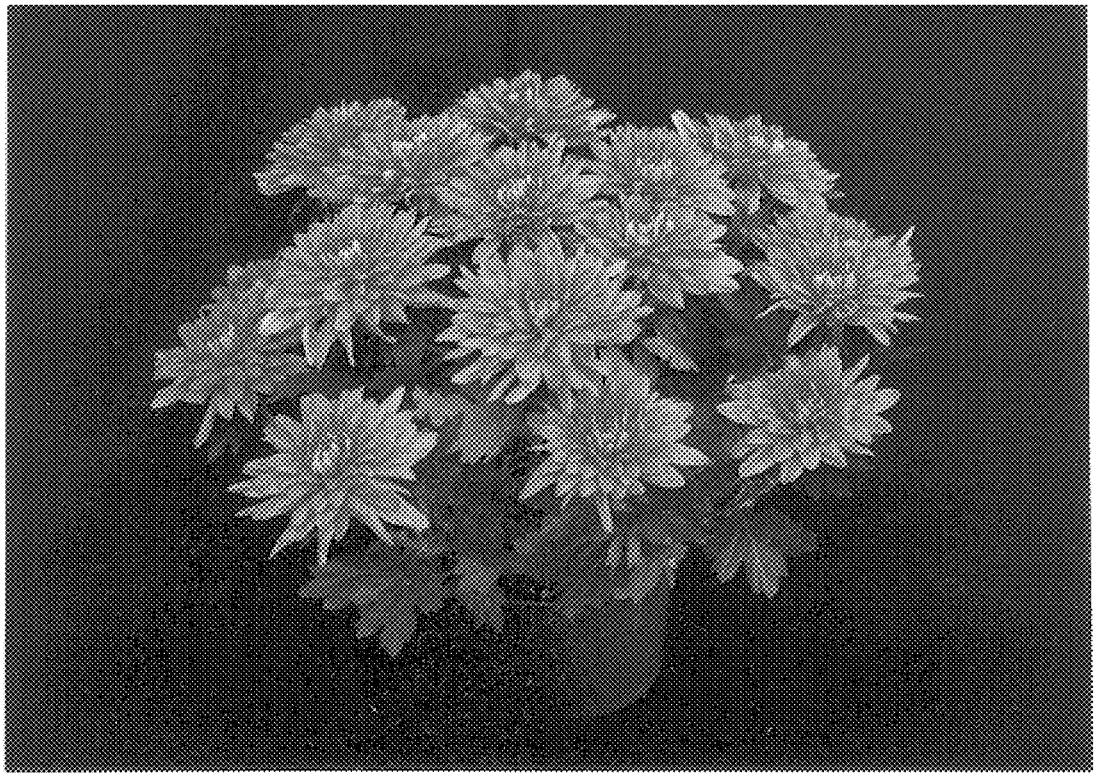
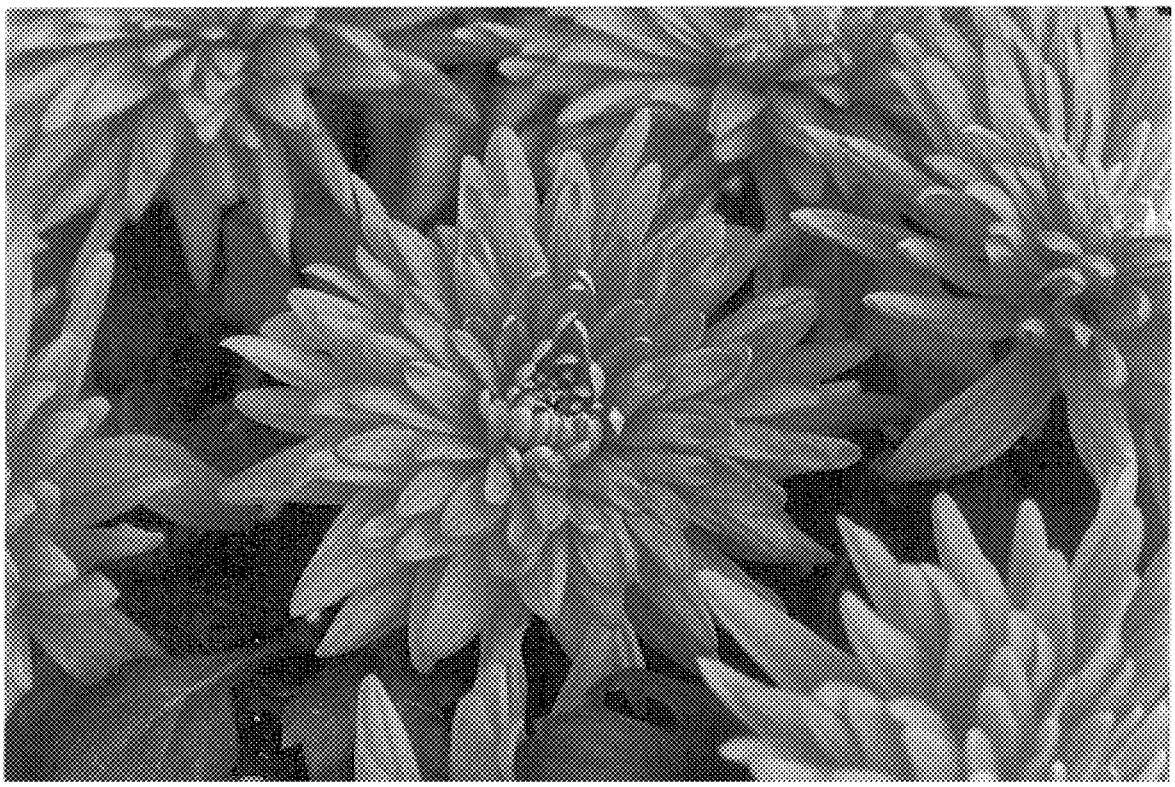

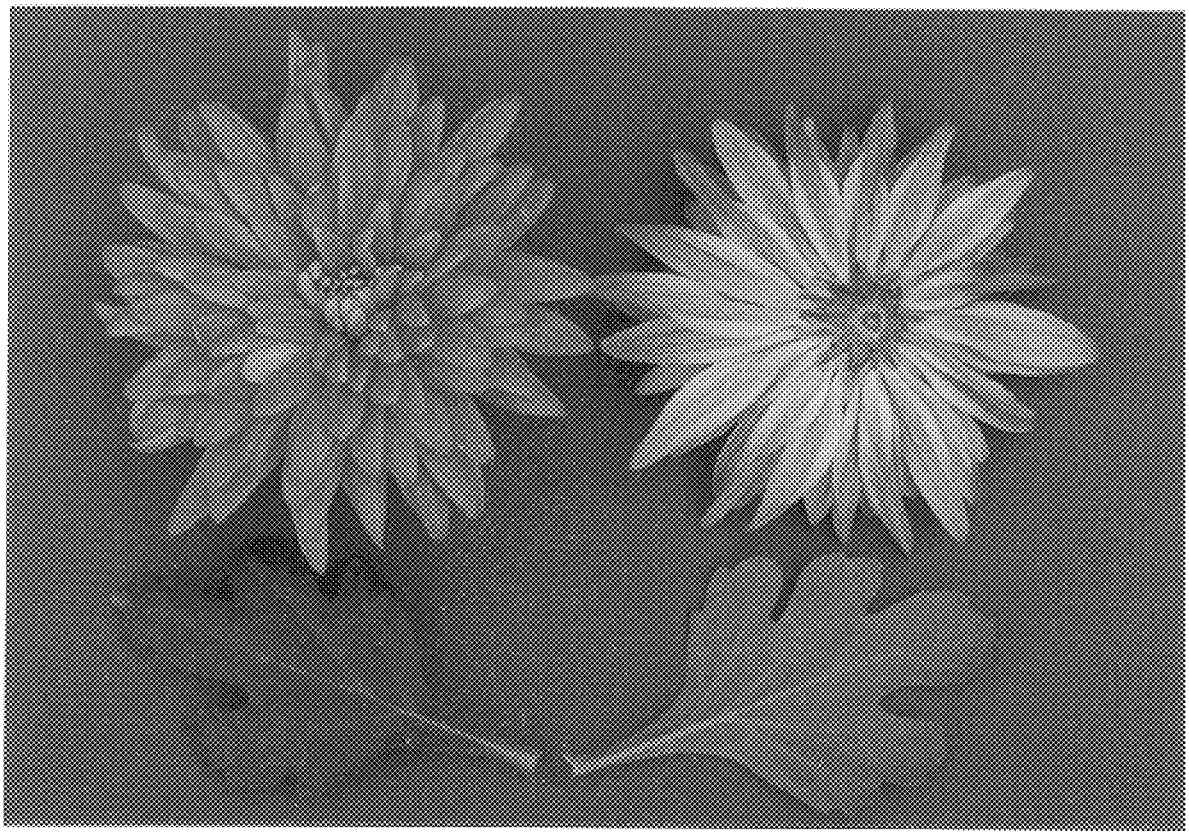
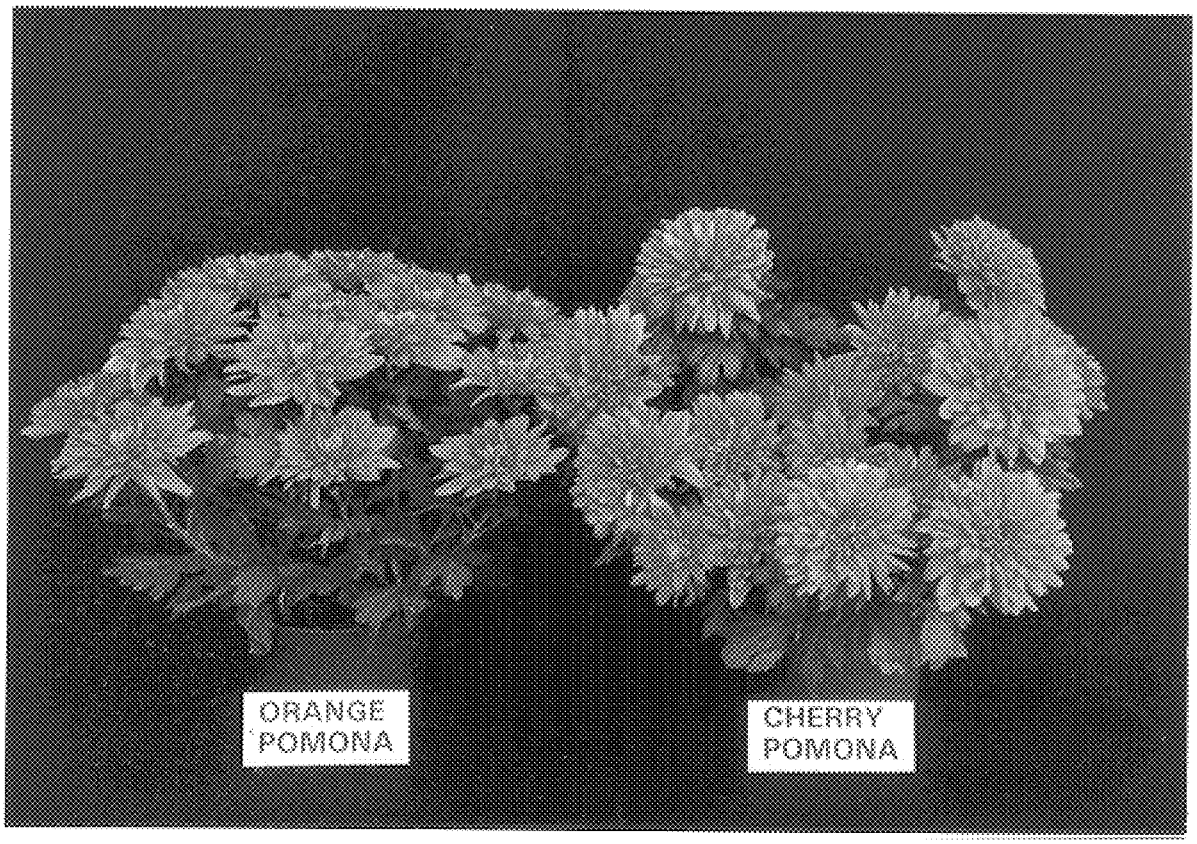
ORANGE
POMONA
CHERRY
POMONA